(12) United States Patent
Homer

(10) Patent No.: US 8,206,379 B2
(45) Date of Patent: Jun. 26, 2012

(54) TECHNIQUES FOR ALTERATION OF IRIS PIGMENT

(76) Inventor: Gregg S. Homer, Sherman Oaks, CA (US)

( * ) Notice: Subject to any disclaimer, the term of this patent is extended or adjusted under 35 U.S.C. 154(b) by 1716 days.

(21) Appl. No.: 10/962,241

(22) Filed: Oct. 8, 2004

(65) Prior Publication Data

US 2005/0049584 A1 Mar. 3, 2005

Related U.S. Application Data

(63) Continuation-in-part of application No. 10/466,963, filed as application No. PCT/US01/29481 on Sep. 20, 2001, now abandoned.

(60) Provisional application No. 60/509,840, filed on Oct. 8, 2003.

(51) Int. Cl.
*A61B 18/18* (2006.01)

(52) U.S. Cl. .................. 606/4; 606/3; 128/898

(58) Field of Classification Search ............ 606/10–14, 606/4–6; 428/403
See application file for complete search history.

(56) References Cited

U.S. PATENT DOCUMENTS

| | | | |
|---|---|---|---|
| 4,461,294 A * | 7/1984 | Baron | 606/5 |
| 5,549,596 A | 8/1996 | Latina | |
| 6,217,171 B1 | 4/2001 | Auten et al. | |
| 6,306,127 B2 | 10/2001 | Homer | |
| 6,428,532 B1 | 8/2002 | Doukas et al. | |
| 6,447,503 B1 | 9/2002 | Wynne et al. | |
| 6,881,249 B2 * | 4/2005 | Anderson et al. | 428/403 |

FOREIGN PATENT DOCUMENTS

| | | | | |
|---|---|---|---|---|
| EP | 1078604 | | 4/1993 | |
| WO | WO01/56518 | * | 8/2001 | 606/4 |

* cited by examiner

*Primary Examiner* — David Shay
(74) *Attorney, Agent, or Firm* — Aka Chan LLP

(57) ABSTRACT

Techniques for altering iris pigment in a human or animal, thereby altering iris color of an iris from a first iris color to a second iris color, are provided. An apparatus includes at least one laser device and a masking device. Another apparatus includes at least one laser device and a contact lens. The at least one laser device can generate at least one beam to selectively remove iris pigment of at least one preselected pigment color from the iris. The energy level of the at least one beam is within a predetermined range. The masking devices include a transparent portion and an opaque portion. The opaque portion of one such masking device occludes a portion of the at least one beam to protect a pupil area. The opaque portion of another such masking device creates an elliptical beam for application of the beam laterally from the side of the iris or some other different angle for lateral exposure of the iris. The contact lens includes a transparent portion and an opaque portion. The opaque portion of such contact lens occludes a portion of the at least one beam to protect a pupil area. In a specific embodiment, the apparatus further includes a second laser device capable of generating a second beam to selectively remove iris pigment of a second preselected pigment color from the iris.

34 Claims, 5 Drawing Sheets

Brown Iris

Green Iris

Fig. 1A
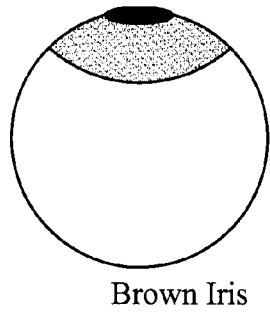
Brown Iris
Fig. 1B
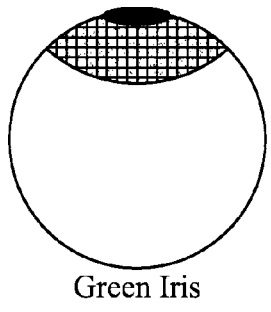
Green Iris
Fig. 1C
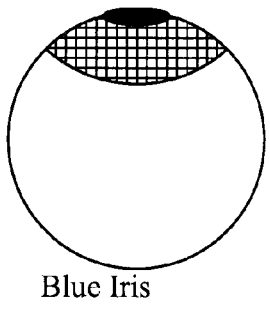
Blue Iris
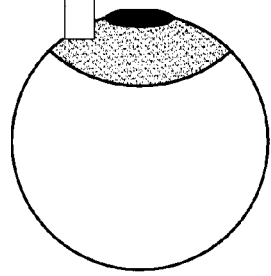
Begin: Brown Iris
Fig. 1D
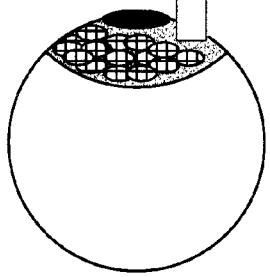
Mid-Treatment
Fig. 1E
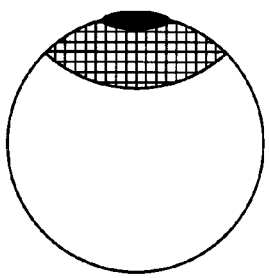
End: Blue Iris
Fig. 1F Fig. 2A
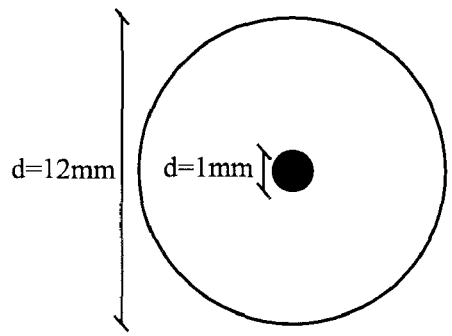
Fig. 2B
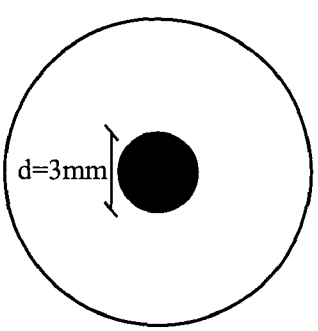
Fig. 2C
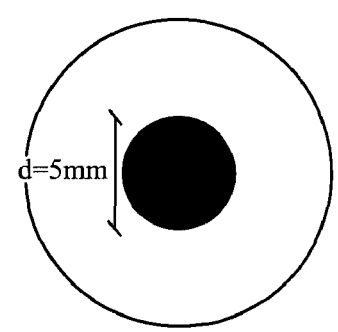
Sample Masks
Fig. 2D
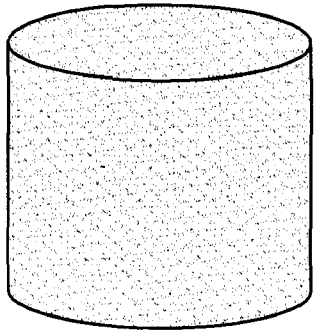
Beam with No Mask
Fig. 2E
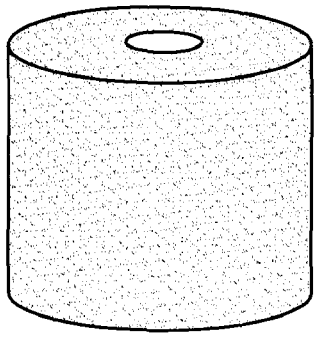
Beam with 3mm Mask
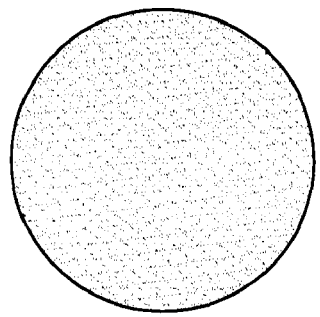
Beam Spot with No Mask
Fig. 2F
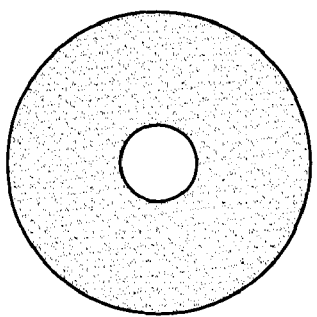
Beam Spot with 3mm Mask
Fig. 2G Fig. 3A
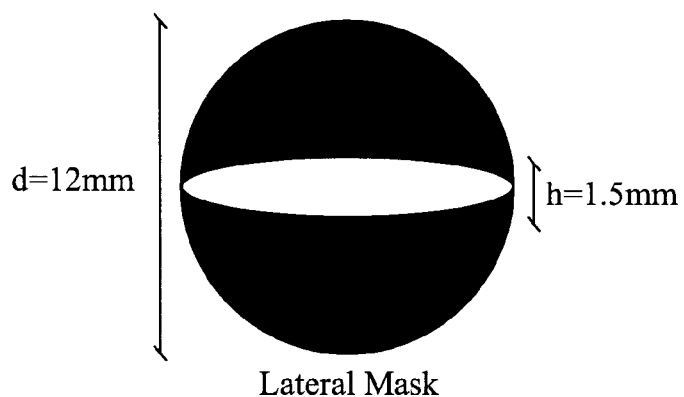
Lateral Mask
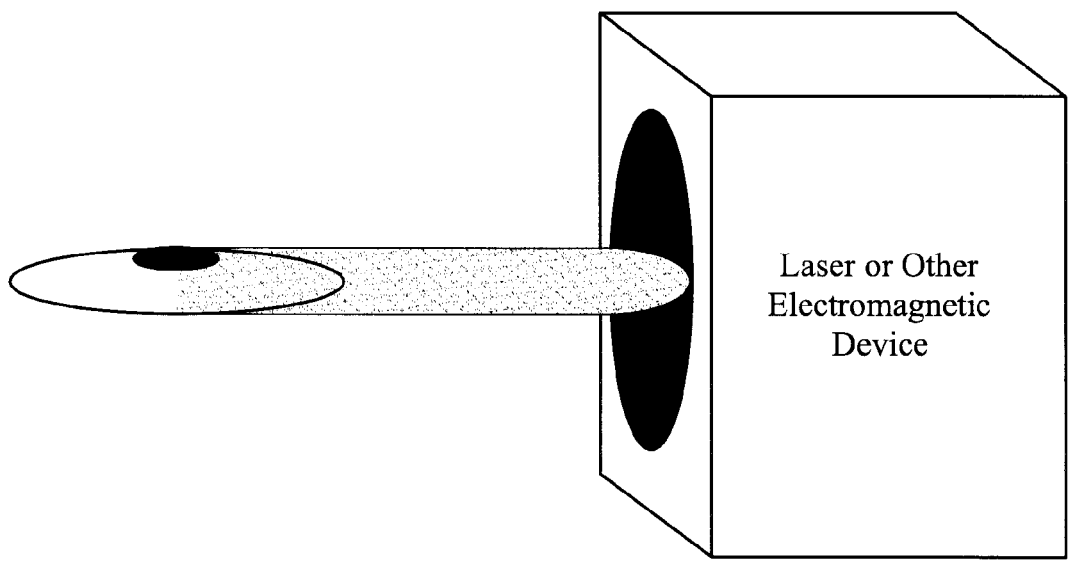
Beam Applied to Human Iris Through Lateral Mask
Fig. 3B

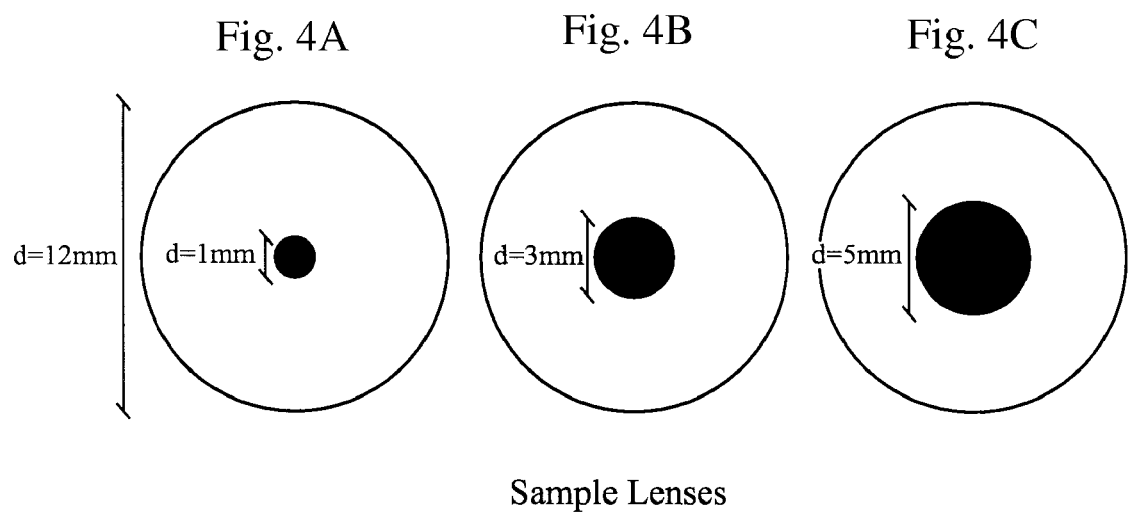
Sample Lenses

TECHNIQUES FOR ALTERATION OF IRIS PIGMENT

CROSS-REFERENCES TO RELATED APPLICATIONS

This application claims the benefit of U.S. provisional patent application 60/509,840, filed Oct. 8, 2003, and is a continuation in part of U.S. patent application Ser. No. 10/466,963, filed Jul. 18, 2003, which is a national stage entry of PCT/US01/29481, filed Sep. 20, 2001, which are all incorporated by reference along with any other references cited in the application.

BACKGROUND OF THE INVENTION

Perceived iris color in humans varies widely between individuals. Iris color of a normal human is dependent on the thickness of collagen fibers on the stroma and the presence and density of colored pigment in the melanin cells of the anterior border layer (or anterior stroma) of the iris. The pigment may exist in more than one form, such as the brown pigment eumelanin and the yellow pigment pheomelanin. These pigments are typically present in both the anterior border layer of the iris and in the deeper epithelial layers of the iris. These pigments may not, however, be evenly distributed between these two layers. For example, pheomelanin may be more prominent in the epithelium than in the anterior border layer.

The stroma consists principally of a network of gray collagen fibers and red capillaries. There is no brown, green or blue in the stroma. The stroma creates the appearance of blue color by refracting the light that passes through its collagen fibers, in much the same way that the refraction of the sun's light by atmospheric molecules creates the appearance of a blue sky (the so-called "Rayleigh scattering"). The thinner the collagen fibers, the more the redness of the capillaries is perceived, producing a violet appearance. The thicker the fibers, the more the grayness of the fibers is perceived, producing a gray appearance. A blue iris is presented in most individuals. Violet and gray irises are rare.

The anterior border layer is anterior to (or in front of) the stroma. The epithelium is posterior to (behind) the stroma. In rare cases, such as albinism, there is no pigment in either the epithelium or the anterior border layer, so the vascular components of the posterior chamber of the eye are revealed, and the iris presents a red or pink color. In most individuals, however, the epithelium is highly pigmented, so the vascular components of the posterior chamber are occluded, but the presence or density of pigment in the anterior border layer varies considerably, so the blue (or gray or violet) light produced by the stroma may or may be fully revealed, partially revealed, or fully occluded. If little or no pigmented is present in the anterior border layer, the blue (or gray or violet) light produced by the stroma is fully revealed, and the perceived iris color is blue (or gray or violet). If the anterior border layer is densely pigmented, the stroma is fully occluded, and the iris appears brown. (In some cases, pigment density is so great that the iris appears almost black in color.) If pigment density is low-intermediate, then the blue light produced by the stroma is only slightly occluded by the yellow-brown melanin cells, and this combination of blue and yellow presents a green iris. If cell density is high-intermediate, then the blue light produced by the stroma is more occluded by the yellow-brown melanin cells, and this combination of blue and yellow-brown presents a hazel (green-brown) iris.

Iris color plays and has played a significant social function as an attribute of beauty. In recent years, alteration of some types of iris color has become possible through the use of colored contact lenses. Such colored contact lenses can have a prescriptive optical power, or can be optically neutral such that the lenses serve as a cosmetic function only.

There are several disadvantages associated with the use of colored contact lenses for cosmetic purposes. First, the lenses have the same potential complications of use as contact lenses with prescriptive optical powers, including allergic reactions to the lens material and infections from improper handling. Further, contact lenses cannot be tolerated by some potential users due to the discomfort. Additionally, colored contact lenses require a degree of dexterity to insert and remove that is not possessed by all potential users. Further, permanent changes in iris color cannot be achieved through the use of colored contact lenses. Moreover, colored contact lenses often fail to provide a natural-looking (and therefore cosmetically acceptable) effect. Whereas natural brown irises are opaque, natural blue (or gray or violet) and green irises are not. When a blue (or gray or violet) and green contact lens is placed over a brown iris, however, an opaque blue (or gray or violet) and green iris is presented. Because this condition does not exist in nature, the iris appears fake and contrived and is not cosmetically appealing.

Another method for altering iris color involves the use of colored lenses implanted anteriorly to the iris. Such implants require an invasive procedure to place the lens in position. Because of the potential complication of an invasive procedure and of leaving a foreign body within the eye, the implantation of color lenses has not become a widely adopted procedure.

Therefore, there remains a need for a method to alter iris pigment in a human which does not require colored contact lenses or implanted lenses. Additionally, there remains a need for techniques to alter iris pigment in a human permanently.

BRIEF SUMMARY OF THE INVENTION

According to one embodiment of the present invention, there is provided a method for altering iris pigment in a human or animal, thereby altering iris color of a first iris from a first iris color to a second iris color. The method comprises, first, selecting one or more than one laser capable of generating one or more than one laser bean that will remove substantially similar amounts of iris pigment of at least two different iris pigment colors from the first iris, and then applying the one or more than one laser beam to the first iris of a first iris color to remove the iris pigment. The removal of the iris pigment causes an alteration in the color of the first iris from the first iris color to the second iris color. The second iris color is substantially the same hue as the first iris color but is less saturated than the first iris color, or the second iris color is both a different hue and less saturated than the first iris color.

In one embodiment, the human or animal is a human patient, and the method further comprises consulting with the patient to determine the second iris color before applying the one or more than one laser beam. In a preferred embodiment, the method further comprises repeating the selecting and applying steps at least one day after applying the one or more than one laser beam. In another preferred embodiment, the method further comprises repeating the selecting and applying steps at after a time between about 1 day and about 2 years after applying the one or more than one laser beam. In a particularly preferred embodiment, the method is repeated at a time between about 1 week and about 1 month after applying the one or more than one laser beam to the iris.

In one embodiment, the second iris color does not naturally occur in a human iris. In another embodiment, the method further comprises creating an opening in the cornea of the human or animal before applying the one or more than one laser beam; and then applying the one or more than one laser beam through the opening. Another embodiment, the one or more than one laser beam generated has a wavelength of between about 50 nanometers and about 2000 nanometers. For example, the wavelength may be from 50 nanometers to 60 nanometers, 60 nanometers to 80 nanometers, 80 nanometers to 100 nanometers, 100 nanometers to 200 nanometers, 200 nanometers to 800 nanometers, 800 nanometers to 1200 nanometers, 1200 nanometers to 1600 nanometers, or 1600 nanometers to 2000 nanometers.

In a preferred embodiment, the method further comprises altering iris pigment in the human or animal, thereby altering iris color of a second iris from a third iris color to a fourth iris color. The method comprises selecting one or more than one laser capable of generating one or more than one laser beam that will remove iris pigment from the second iris, and then, applying the one or more than one laser beam to the second iris of the third iris color to remove iris pigment. The removal of the iris pigment of the second selected color causes an alteration in the color of the second iris from the third iris color to the fourth iris color. In a particularly preferred embodiment, the second iris color is substantially the same as the fourth iris color. In another particularly preferred embodiment, the second iris color is substantially different from the fourth iris color.

In another embodiment, an iris pigment alteration apparatus is provided. The apparatus includes at least one laser device and a beam masking device. The at least one laser device can generate at least one beam to selectively remove iris pigment of at least one preselected pigment color from the iris. The energy level of the at least one beam is within a predetermined range. The beam masking device includes a transparent portion and an opaque portion. In one such embodiment, the opaque portion forms a reverse grommet pattern and occludes a portion of the at least one beam to protect a pupil area. (See FIGS. 2A, 2B, 2C, 2E, and 2G.) In another such embodiment, the opaque portion forms a narrow elliptical beam for treatment of the iris laterally (from the side) or from some different angle other than perpendicular to the iris. (See FIGS. 3A and 3B.) In a specific embodiment, the apparatus further includes a second laser device capable of generating a second beam to selectively remove iris pigment of a second preselected pigment color from the iris.

In yet another embodiment, a protective pupil contact lens is provided. The contact lens, contoured to uniformly rest on a surface of the eye, includes a circular, opaque portion, forming a reverse grommet pattern, the opaque portion having a size about that of a pupil area of an eye. The opaque portion prevents an electromagnetic beam directed towards the eye from entering the pupil area. (See FIG. 4.) The laser beam can have a wavelength of between 50 nanometers to about 2000 nanometers, and have sufficient energy to destroy (by bursting or killing off) pigmented cells of an iris.

Various additional objects, features, and advantages of the present invention can be more fully appreciated with reference to the detailed description and accompanying drawings that follow.

BRIEF DESCRIPTION OF THE DRAWINGS

FIGS. 1A-1F show side views of an embodiment of the present invention, using the beam and spot produced by existing laser devices.

FIGS. 2A, 2B, and 2C show front views of sample reverse grommet masks.

FIG. 2D shows the side view of a beam with no reverse grommet mask, and FIG. 2E shows the side view of a beam with a 3 millimeter reverse grommet mask.

FIG. 2F shows the top view of a beam spot with no reverse grommet mask, and FIG. 2G shows the top view of a beam spot with a 3 millimeter reverse grommet mask.

FIG. 3A shows the front view of a lateral mask.

FIG. 3B shows a beam being applied to a human iris though a lateral mask.

FIGS. 4A-4C show aspects of an embodiment of the present invention using the reverse grommet contact lens.

DETAILED DESCRIPTION OF THE INVENTION

Figure 5:
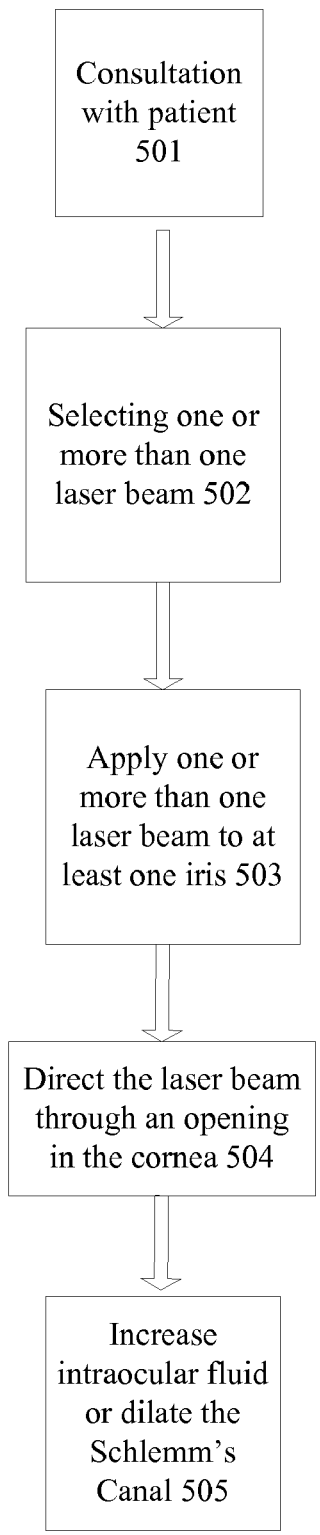
FIG. 5 shows one embodiment of the present invention.

According to one embodiment of the present invention, there is provided a method for removing iris pigment in a human, and thereby altering perceived iris color from a first iris color to a second iris color. In one embodiment, the method comprises selecting one or more than one laser capable of generating one or more than one laser beam that will selectively remove iris pigment substantially of only a first pigment color, or that will remove iris pigment substantially uniformly of all iris pigment colors to decrease the overall density of all colors of iris pigment, or that will remove iris pigment of a first pigment color and a second pigment color while removing more iris pigment of the first pigment color than iris pigment of the second pigment color. Next, the one or more than one laser beam is applied to an iris of a first iris color to remove iris pigment. The removal of iris pigment causes an alteration in the color of the iris from the first iris color to the second iris color, where the second iris color is a different hue than the first iris color, or is a different saturation than the first iris color or is both a different hue and a different saturation than the first iris color. The method will now be explained in greater detail.

As used in this disclosure, "laser," means any form of electromagnetic radiation, whether in the form of sound, heat, light, or otherwise, and whether consisting of radio frequency, microwave, infrared, visible light, ultraviolet light, x-ray, t-ray, gamma ray, or otherwise. The term "laser" is not intended to restrict the form of radiation in terms of monochromaticity (i.e., composed of one or more than one different wavelength), directionality (i.e., produce a single nondivergent spot or radiate in several different directions), or coherence (i.e., the waves produced consist of a single phase relation or of multiple phase relations). Nor is there any intention to limit the method to a particular pulse rate. The rate can be continuous (i.e., nonpulsed) or pulsed, and if pulsed, it can be pulsed at any rate (such as, in microseconds, nanoseconds, picoseconds, or femtoseconds). Nor is there any intention to limit the patent to any particular spot shape, size, or angle of projection. The spot is the area of the plane produced on the surface of the target by the laser, and its size and shape can vary, depending upon the desired effect. The angle of projection can influence the effect of the laser as well, including the nature and degree of penetration and the corresponding impact on posterior tissue. In one embodiment, the laser spot has a small diameter (such as, 3 microns) and is fired in rapid succession while moving across the entire surface of the iris, with the angle of the beam either perpendicular to the iris surface or at any angle thereto. (See FIGS. 1A-1F.) In another embodiment, the spot is circular in shape and has a large diameter (such as, 1 centimeter) covering the entire surface of the iris and is fired only one time or multiple times from the same position perpendicular to the iris. (See FIGS. 2A-2G.)

In this embodiment, the pupil will be protected from the laser by a masking device with a spot of opaque material in the center to occlude the laser beam. A set of these masking devices (or a single adjustable mask) will be available with a variety of opaque regions sufficient to accommodate variations in pupil size (such as diameters of 0.5 millimeters through 5 millimeters). Pupil size may vary depending on the individual and the conditions. For example, under darkened conditions the pupil size may be larger than in brightened conditions. Furthermore, the pupil may be altered using a particular substance, such as a medication to contract the pupil. In another embodiment, the pupil will be protected from the laser by a contact lens with a spot of opaque material in the center to occlude the laser beam. A set of these contact lenses will be available with a variety of opaque regions sufficient to accommodate variations in pupil size (such as diameters of 0.5 millimeters through 5 millimeters). In another embodiment, a masking device produces a spot is in the shape of an ellipse, and is fired from each side of the eye, either pulsed or continuous. (See FIGS. 3A and 3B.) These embodiments are not intended to be exhaustive or exclusive.

According to another embodiment of the present invention, there is provided a method for altering the iris pigment in the iris of an animal or a human to change the color of the iris from a first iris color to a second iris color. The method of the present invention is performed as follows. First, the human patient or animal is examined and, if a human patient, a determination is made in consultation with the human patient as to patient's desired iris color. Next, a determination is made as to whether the patient's desired iris color can be obtained using the method of the present invention by virtue of laser alteration of the patient's existing iris pigment as will be understood by those in the art with reference to this disclosure. For example, if the patient has brown irises and desires to have green irises, then laser alteration of the patient's iris pigment using the present method can alter the patient's irises to green. Similarly, if the patient has brown irises and desires less saturated brown irises, then laser alteration of the patient's iris pigment using the present method can alter the patient's irises to less saturated brown irises. Further, if the patient has brown irises and desires to have green irises that are also less saturated, then laser alteration of the patient's iris pigment using the present method can alter the patient's irises to less saturated green irises. If, however, the patient has blue irises and desires to have brown irises, then laser alteration of the patient's iris pigment using the present method cannot alter the patient's irises to brown, as will be understood by those in the art with reference to this disclosure.

Next, the method comprises selecting one or more than one laser capable of generating one or more than one laser beam. Depending on the first iris color and the desired second iris color, as will be understood by those in the art with reference to this disclosure, the one or more than one laser beam is selected that will either selectively remove iris pigment substantially of only a first selected pigment color, or that will remove iris pigment substantially uniformly of all iris pigment colors to decrease the overall density all colors of iris pigment, or that will remove iris pigment of a first pigment color and a second pigment color while removing more iris pigment of the first pigment color than iris pigment of the second pigment color.

For example, if the second iris color is the substantially the same hue but less saturated than the first iris color, than the one or more than one laser is selected that will remove iris pigment substantially uniformly of all iris pigment colors to decrease the overall density of all colors of iris pigment. Alternately, if the second iris color is a different hue than the first iris color, than the one or more than one laser is selected that will selectively remove iris pigment substantially of only a first selected pigment color. Similarly, if the second iris color is both a different hue and less saturated than the first iris color, than the one or more than one laser is selected that will remove iris pigment of a first pigment color and a second pigment color while removing more iris pigment of the first pigment color than iris pigment of the second pigment color, depending on the first iris color and the desired second iris color, as will be understood by those in the art with reference to this disclosure.

Next, the one or more than one laser beam is applied to the iris of the first iris color at a sufficient intensity and for a sufficient time to remove iris pigment, where the removal of the iris pigment causes an alteration in the color of the iris from the first iris color to the second iris color. If more than one laser beam is used, the laser beams can be applied sequentially or simultaneously. The second iris color is a different hue than the first iris color, or is substantially the same hue as the first iris color but less saturated than the first iris color, or both are a different hue and less saturated than the first iris color. Further, it is possible using methods according to the present invention to alter iris pigment of a patient to result in an iris color which is not naturally occurring, or to alter iris pigment differently between two eyes of a patient to result in the patient having irises of different colors by differentially treating each iris of a patient according to one method of the present invention or by treating only one iris of the patient according to the present invention.

Preferably, the intensity of the laser beam is set to a level that minimizes the damage to any ocular tissue while still allowing satisfactory removal of the required iris pigment. The method of the present invention can further include creating an opening in the cornea of the human before applying the one or more than one laser beam, and then applying the one or more than one laser beam through the opening in order to minimize damage to the anterior ocular structures. If necessary, a temporary contact lens can be applied to reduce post-procedure discomfort.

Additionally, the method of the present invention can be repeated at a time spaced apart from the original application of the one or more than one laser, in order to further alter the iris pigment, after allowing the iris and associated tissue to heal from the original application. For example, the method can be repeated at least one day after applying the one or more than one laser beam to the iris. In a preferred embodiment, the method is repeated at a time between about 1 day and about 2 years after applying the one or more than one laser beam to the iris. In a particularly preferred embodiment, the method is repeated at a time between about 1 week and about 1 month after applying the one or more than one laser beam to the iris.

The use of lasers to remove iris pigment is advantageous because specific lasers can be selected which create laser beams which are selectively absorbed by iris pigment of specific colors. In one embodiment, this property allows the selection of lasers to selectively destroy (such as, by bursting or killing off) the pigmented cells of the anterior border layer without destroying the non-pigmented cells of the cornea, stroma, endothelium, or epithelium. In another embodiment, it allows the selection of lasers to shut off of form of melanin (such as, eumalanin) without shutting off another (such as, pheomelanin). Alternately, one or more than one laser beam can be selected to remove iris pigment substantially uniformly of all iris pigment colors to decrease the overall density all colors of iris pigment. Additionally, the one or more than one laser beam can be selected to remove iris pigment of a first pigment color and a second pigment color while removing more iris pigment of the first pigment color than iris pigment of the second pigment color.

In a preferred embodiment, the one or more than one laser selected is a pulse dye laser because the wavelength of the laser beam is determined by the color of the material through which the laser beams pass. This advantageously increases the specificity of iris pigment destruction by the laser beams by selecting appropriate dyes. Moreover, the intensity of the laser beams can be adjusted to minimize damage to ocular tissue and iris pigments that are not specifically targeted. In another preferred embodiment, the one or more than one laser is a pulse dye laser and the wavelength generated by the one or more than one laser is between about 300 nanometers and about 1000 nanometers. For example, suitable lasers include the Due-220, DUO-221, and the DUO-210 models, as well as the DYE 120, the DYE 121, and the DYE 110 models (Laser Science, Inc., Franklin, Mass. US). Another candidate is the PhotoGenica V-Star Pulsed Dye Laser (Cynosure, Inc., Chelmsford, Mass., USA), with wavelength of 585 nanometers.

In another preferred embodiment, the one, or more than one laser selected, is an Nd:YAG laser, such as the Nd:YAG infrared laser with a wavelength of 1064 nanometers (like the Diode Pumped Infrared CrystaLaser, Model No: IRCL-1064-300-S, from CrystaLaser, Reno, Nev., USA) or the frequency doubled Nd:YAG visible (green) laser, with a wavelength of 532 nanometers (like the Diode Pumped Green CrystaLaser, Model No: GCL-050-L, also from CrystaLaser, Reno, Nev., USA).

The pulse rate can also vary. In another preferred embodiment, a femtosecond-pulsed laser is used which permits the operator to focus the laser energy on a specific depth of penetration. For example, the IntraLase femtosecond laser uses a long wavelength (1053 nanometers) that is not absorbed, but instead passes through the cornea with minimal effect on tissue until it reaches the pre-programmed target. (IntraLase Corp., Irvine, Calif., US.) The femtosecond laser pulses are placed close together to define precise subsurface areas of photodisruption.

Iris pigment can be removed in a variety of ways. One way is to kill off the pigmented cells and wait for the organism to eliminate the dead cells. Another way is to burst the pigmented cells and wait for the organism to eliminate the free melanin. Killing off the cells will require less energy than bursting the cells, but the organism will require more time to eliminate dead cells than free melanin. In addition a laser could simply shut off the melanin without killing or bursting the pigmented cells. In this case, no elimination would be required. Moreover, it is possible to shut off one melanin pigment (such as, eumalanin) without shutting off another (such as, pheomelanin), thereby further influencing the modified color of the iris.

In another preferred embodiment of the present invention, prior to the procedure, the patient's iris is stretched by contracting the patient's pupil using a 0.01 percent carbachol optic solution (such as Miostat from Alcon Inc., Humacao, Puerto Rico, USA).

In still another preferred embodiment of the present invention, after the pigmented cells are killed off or burst, metabolization or elimination of the free melanin or cell die-off is accelerated by increasing the production of intraocular fluid, dilating the Schlemm's Canal, or both. Intraocular fluid production can be increased by stimulating the patient's nervous system with 36 milligrams of methylphenidate (such as Concerta from ALZA Corporation, Mountain View, Calif., USA) or 40 milligrams of dextroamphetamine sulfate (such as Dexedrine from GlaxoSmithKline, Brentford, England). Intraocular fluid production can also be accelerated by dilating the patient's pupil with a 1 percent tropicamide optic solution (such as Mydriacyl from Alcon Inc., Humacao, Puerto Rico, USA) or a 2.5 percent phenylephrine hydrochloride optic solution (such as AK-Dilate from Akorn, Inc., Abita Springs, La.). The patient's Schlemm's canal can be dilated with a 0.1 percent adrenergic optic solution (such as Propine from Allergan Inc., Irvine, Calif. USA), a 0.15 percent docosanoid (such as Rescula from Novartis Opthalmics, Bulach, Switzerland), or a 0.0004 percent prostaglandin analog (such as Xalatan from Pfizer Inc., New York, N.Y., USA).

By reducing pigment density in the anterior border layer, more of the stroma's blue light refraction is allowed to show through. If pigment density of a brown eye is reduced, for example, then the eye will present as hazel, green, blue, or baby blue, depending upon the extent to which the pigment density has been so reduced.

The violet eye is a product of both reduced pigment density and thin stromatic collagen. The stroma consists primarily of gray collagen fibers and red capillaries. In the typical stroma, the stroma reads blue. When the fibers are thinner, however, more of the capillaries are revealed, and the iris reads more violet. And when these fibers are thicker, the iris reads more gray. When the pigment density is reduced or the melanin is shut off, this blue, violet, or gray is presented. The reduction of pigment density by bursting or killing the pigmented cells is, by definition, damage to the ocular tissue. The goal is to minimize damage to any adjacent ocular tissue. This can be accomplished by varying the energy, wavelength, and/or pulse rate of the laser. By using a lower energy output, less collateral damage will occur. By using a longer wavelength, less penetration will occur. And by increase pulse rate, the energy will dissipate before it has the opportunity to spread to adjacent tissues. In addition, some laser can actually focus to a specified depth of penetration. The femtosecond laser has this capability. As a result, energy can be focused on the anterior stroma (or anterior border layer) without damaging the more anterior corneal layer or the more posterior stromatic or endothelial layers.

In an embodiment of the invention, one or more lasers are used to achieve a violet colored iris from an iris of another color. Typically, violet is any group of colors of reddish blue hue, low lightness, and medium saturation.

In one embodiment, this property allows the selection of lasers to selectively destroy (e.g., by killing or bursting) the pigmented cells of the anterior stroma or border layer without destroying the non-pigmented cells of the cornea, stroma, endothelium, or epithelium. In another embodiment, it allows the selection of lasers to shut off of form of melanin (e.g., eumalanin) without shutting off another (e.g., pheomelanin).

In another preferred embodiment, the one, or more than one laser selected, is a femtosecond laser which permits the operator to focus the laser energy on a specific depth of penetration. For example, the IntraLase femtosecond laser uses a long wavelength (1053 nanometers) that is not absorbed, but instead passes through the cornea with minimal effect on tissue until it reaches the pre-programmed target. (IntraLase Corp., Irvine, Calif., US.) The femtosecond laser pulses are placed close together to define precise subsurface areas of photodisruption.

In another embodiment of the present invention, an optical scanning device can be used to map iris pigmentation prior to, during, or after alteration of iris pigmentation, or any combination of these. Similarly, an optical positioning or guidance device can also be used to guide an electromagnetic radiation device (such as a laser) along a surface of an iris. The optical scanning device or the optical positioning device, or both, can be implemented using one or more computer systems. An exemplary computer system can include software, monitor, cabinet, keyboard, and mouse. The cabinet can house familiar computer components, such as a processor, memory, mass storage devices, and the like. Mass storage devices may include mass disk drives, floppy disks, Iomega ZIP™ disks, magnetic disks, fixed disks, hard disks, CD-ROMs, recordable CDs, DVDs, DVD-R, DVD-RW, Flash and other non-volatile solid-state storage, tape storage, reader, and other similar media, and combinations of these. A binary, machine-executable version, of the software of the present invention may be stored or reside on mass storage devices. Furthermore, the source code of the software of the present invention may also be stored or reside on mass storage devices (e.g., magnetic disk, tape, or CD-ROM). Furthermore, a computer system can include subsystems such as central processor, system memory, input/output (I/O) controller, display adapter, serial or universal serial bus (USB) port, network interface, and speaker. The present invention may also be used with computer systems with additional or fewer subsystems. For example, a computer system could include more than one processor (i.e., a multiprocessor system) or a system may include a cache memory.

EXAMPLE 1

One method of the present invention is performed as follows: An adult male patient is selected who desires to change his perceived iris color permanently from brown to blue. The patient is found in satisfactory general and ocular health. After being counseled regarding the procedure and being prepared, a suitable laser is selected and is applied to each iris through the patient's intact corneas to burst the melanin cells in the anterior border layer of patient's irises. The free melanin is then cleared through the patient's metabolism or eliminated through the patient's Schlemm's canal until the stroma is fully exposed, presenting a perceived iris color of blue.

FIG. 5 shows an embodiment of the present invention. After consultation with a patient 501, a practitioner selects at least one laser beam 502 to apply to at least one iris 503. In one embodiment, the laser beam is directed through an opening in the cornea 504. To accelerate metabolization or elimination of the free melanins or cell die-off, the practitioner may increase the intraocular fluid or dilate the Schlemm's Canal or both 505.

One of ordinary skill in the art would recognize many other variations, modifications, and alternatives. The above examples are merely illustrations, which should not unduly limit the scope of the claims herein. It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method to alter perceived iris color of an iris from a first iris color to a second iris color, the method comprising:
providing an electromagnetic radiation device capable of generating a first beam to selectively remove iris pigment, comprising at least one of eumelanin or pheomelanin, of a first pigment color from the iris of an eye;
protecting a pupil region of the eye; and
directing the first beam towards the iris, thereby altering at least one of iris color, hue, or saturation.

2. The method of claim 1 further comprising:
providing a second electromagnetic radiation device capable of generating a second beam to selectively remove iris pigment of a second preselected pigment color from the iris, the first preselected pigment color being different from the second preselected pigment color; and
directing the second beam towards the iris, thereby altering at least one of iris color, hue, or saturation.

3. The method of claim 1 wherein the protecting and the directing are repeated at least once after a period of time.

4. The method of claim 3 wherein the period of time ranges from about one day to about two years.

5. The method of claim 1 wherein the electromagnetic radiation device is a pulse dye laser.

6. The method of claim 1 wherein the electromagnetic radiation device is a Nd:YAG infrared laser.

7. The method of claim 1 wherein the electromagnetic radiation device is a frequency doubled Nd:YAG visible (green) laser.

8. The method of claim 1 wherein first beam comprises at least one of ultrasound waves, microwaves, radio frequency waves, infrared rays, visible rays, ultraviolet light rays, x-rays, gamma rays, or t-rays, or combinations thereof.

9. A method for altering iris pigmentation, comprising at least one of eumelanin or pheomelanin, in a human, thereby altering perceived iris color of a first iris from a first iris color to a second iris color, the method comprising:
applying one or more than one laser beam to the first iris of a first iris color to remove iris pigment of a first preselected pigment color,
wherein the removal of the iris pigment of the first preselected color causes an alteration in the iris color of the first iris from the first iris color to the second iris color.

10. The method of claim 9 wherein the second iris color is a different hue than the first iris color.

11. The method of claim 9 wherein the second iris color is substantially the same hue as the first iris color but less saturated than the first iris color.

12. The method of claim 9 wherein the second iris color is substantially a different hue than the first iris color and less saturated than the first iris color.

13. The method of claim 9 wherein the hue of the second iris color is a hue that does not naturally occur in a human iris.

14. The method of claim 9 wherein the second iris color is violet.

15. The method of claim 9 wherein the one or more than one laser preselected is a pulse dye laser.

16. The method of claim 9 wherein the one or more than one laser preselected is a Nd:YAG infrared laser.

17. The method of claim 9 wherein the one or more than one laser preselected is a frequency doubled Nd:YAG visible (green) laser.

18. The method of claim 9 wherein the one or more than one laser beam generated has a wavelength of between about 50 nanometers and about 2000 nanometers.

19. The method of claim 9 further comprising altering iris pigmentation, comprising at least one of eumelanin or pheomelanin, in the human, thereby altering perceived iris color of a second iris from a third iris color to a fourth iris color, the method comprising:
applying the one or more than one laser beam to the second iris of the third iris color to remove iris pigment of the second preselected pigment color, wherein the removal of the iris pigment of the second preselected color causes an alteration in the color of the second iris from the third iris color to the fourth iris color.

20. The method of claim 9 further comprising repeating the applying.

21. The method of claim 9 wherein the second iris color is substantially same as the fourth iris color.

22. The method of claim 9 wherein the second iris color is substantially different than the fourth iris color.

23. The method of claim 9 further comprising at least one of increasing a flow of intraocular fluid or dilating a Schlemm's canal, or a combination of both.

24. The method of claim 9 further comprising protecting a pupil from the one or more than one laser beam, wherein the protecting is accomplished by at least one of an occlusive contact lens or an occlusive mask coupled to the one or more than one laser.

25. The method of claim 9 wherein an occlusive mask is coupled to the one or more than one laser to alter a shape of the one or more than one laser beam.

26. The method of claim 25 wherein the applying of the one or more than one laser beam to the first iris is directed at a lateral angle.

27. The method of claim 9 wherein the one or more than one laser beam has a diameter of about a diameter of the iris.

28. The method of claim 9 wherein the one or more than one laser beam has a diameter of less than a diameter of the iris.

29. The method of claim 28 further comprising applying the one or more than one laser beam to a plurality of regions of the iris.

30. The method of claim 9 further comprising applying a miotic solution to an eye to stretch the first iris.

31. The method of claim 9 wherein iris pigment is removed by at least one of killing pigmented cells or bursting pigmented cells.

32. The method of claim 9 wherein the one or more than one laser beam is continuous.

33. The method of claim 9 wherein the one or more than one laser beam is pulsed.

34. The method of claim 33 wherein the one or more than one laser beam has pulse rate period ranging from about 1 femtosecond to about 1 second.

* * * * *